(12) United States Patent
Nakajima et al.

(10) Patent No.: US 7,968,588 B2
(45) Date of Patent: Jun. 28, 2011

(54) INJECTABLE FORMULATION OF ANTIBIOTIC AND SOLUTION FOR INTRAVENOUS ADMINISTRATION THEREOF

(75) Inventors: Hirofumi Nakajima, Tokyo (JP); Haruhiko Machida, Tokyo (JP)

(73) Assignee: eRigen Pharmaceuticals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 12/306,663

(22) PCT Filed: Jun. 28, 2007

(86) PCT No.: PCT/JP2007/063003
§ 371 (c)(1),
(2), (4) Date: Feb. 12, 2009

(87) PCT Pub. No.: WO2008/001849
PCT Pub. Date: Jan. 3, 2008

(65) Prior Publication Data
US 2009/0258920 A1    Oct. 15, 2009

(30) Foreign Application Priority Data

Jun. 29, 2006   (JP) ................................ 2006-179778

(51) Int. Cl.
*A61K 31/403* (2006.01)
*A61P 31/04* (2006.01)
(52) U.S. Cl. ...................................................... 514/414
(58) Field of Classification Search .................... 514/414
See application file for complete search history.

(56) References Cited

U.S. PATENT DOCUMENTS

| | | | |
|---|---|---|---|
| 5,648,455 | A | 7/1997 | Ohashi et al. |
| 6,869,927 | B1 | 3/2005 | Gentz et al. |
| 2003/0220237 | A1 | 11/2003 | Ohnaka et al. |
| 2004/0072797 | A1 | 4/2004 | Aramwit et al. |
| 2005/0187249 | A1 | 8/2005 | Fuji et al. |
| 2005/0239692 | A1 | 10/2005 | Lindenblatt et al. |
| 2006/0111432 | A1 | 5/2006 | Lee et al. |

FOREIGN PATENT DOCUMENTS

| | | | |
|---|---|---|---|
| EP | 0 838 225 A2 | | 4/1998 |
| JP | 8-000273 A | | 1/1996 |
| JP | 10-139663 A | | 5/1998 |
| JP | 2003-500456 A | | 1/2003 |
| JP | 2003-183154 A | | 7/2003 |
| JP | 2003321364 A | * | 11/2003 |
| JP | 2005-534671 A | | 11/2005 |
| JP | 2006-143699 A | | 6/2006 |
| WO | WO 00/62793 A2 | | 10/2000 |
| WO | WO 03/094889 A1 | | 11/2003 |

OTHER PUBLICATIONS

Form PCT/ISA/210 (International Search Report) dated Jul. 31, 2007.

(Continued)

*Primary Examiner* — James Anderson
*Assistant Examiner* — Zohreh Vakili
(74) *Attorney, Agent, or Firm* — Buchanan Ingersoll & Rooney, P.C.

(57) ABSTRACT

A pharmaceutical composition for injection comprising a depsipeptide antibiotic, WAP-8294A$_2$, as an active ingredient, which is stable and contains WAP-8294A$_2$ in high concentrations is provided. This composition comprises WAP-8294A$_2$ of the following structural formula (1) as an active ingredient and is characterized in that 2-hydroxypropyl-β-cyclodextrin or β-cyclodextrin is contained as a stabilizer or solubilizer and the pH of the composition is not adjusted. This composition is mixed with a pH-adjusting agent such as dextrose and with an infusion or diluent comprising a solution of disodium hydrogen phosphate, sodium dihydrogen phosphate, and sodium hydroxide at the time of use to prepare a solution for intravenous administration of WAP-8294A$_2$.

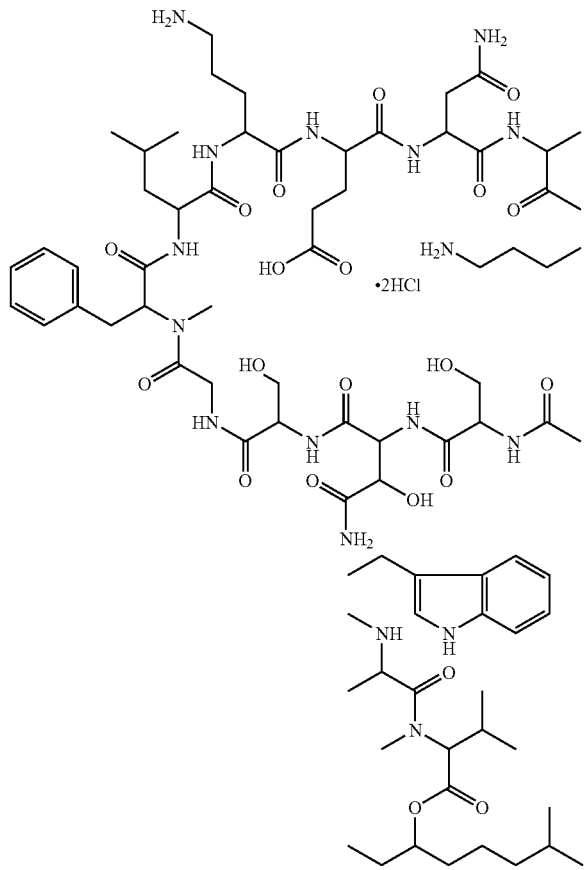

(1)

18 Claims, No Drawings

OTHER PUBLICATIONS

Form IPEA/409 (International Preliminary Report on Patentability) dated Apr. 25, 2008.

K. I. Harad et al., "Separation of WAP-8294A Components, A Novel Anti-Methicillin-Resistant Staphylococcus Aureus Antibiotic, Using High-Speed Counter-Current Chromatography", J. Chromatogr A, 2001, vol. 932, No. 1-2, pp. 75-81, Abstract.

SupplementaryEuropean Search Report for EP 07 767796 (corresponding to PCT/JP2007/063003) dated Apr. 23, 2010.

Viles et al., (1996) "Multiple solution conformation of the integrin-binding cyclic pentapeptide cyclo(-Ser-$_D$-Leu-Asp-Val-PRO-)," Eur J Bioche. 242:352-362.

Sanderson et al., (1994) "Characterization of the solution conformation of a cyclic RGD peptide analogue by NMR spectroscopy allied with a genetic algorithm approach and constrained molecular dynamics," Int J Pept Protein Res. 43(6)588-596.

Locardi et al., (1999) Conformations and pharmacophores of cyclic RGD containing peotides which selectively bind integrin alpha$_v$, beta$_3$, J Peptide Sci. 5(11):491-506.

\* cited by examiner

INJECTABLE FORMULATION OF ANTIBIOTIC AND SOLUTION FOR INTRAVENOUS ADMINISTRATION THEREOF

TECHNICAL FIELD

The present invention relates to an injectable formulation for extemporaneous preparation of a depsipeptide antibiotic, WAP-8294A, which has a marked antibacterial activity against methicillin-resistant *Staphylococcus aureus*(MRSA), a solution for intravenous administration thereof, and methods for preparation thereof.

BACKGROUND ART

MRSA is drug-resistant *Staphylococcus aureus* against which antibiotics including methicillin have been ineffective. The emergence of MRSA was first reported in 1961 in England, and thereafter MRSA spread rapidly across the world. Nowadays MRSA comprises 50-70% of *Staphylococcus aureus* isolated in medical facilities, and is rampant in hospitals. Health care providers and patients are easy to infect with MRSA by contact within medical facilities. Usually healthy persons become just carriers when infected with MRSA because MRSA itself is a variant of *Staphylococcus aureus* and has low pathogenicity. On the other hand, when aged persons with reduced immunity, patients with immunodeficiency, post-operative patients, or patients having an intubated catheter in the trachea or a blood vessel are infected with MRSA, it proliferates within the body to cause various infectious diseases such as pneumonia, enteritis, septicemia, endocarditis, and meningitis. In the West and in Japan where medical care is highly developed, MRSA infections are regarded as one of the most serious infections in medical facilities, and require various countermeasures for prevention of its infections.

Since there is no apparent difference in symptoms and progress between MRSA infections and other bacterial infections, MRSA infections are very difficult to distinguish by general clinical findings and laboratory test values. The diagnosis is confirmed by identification of MRSA by microbiological examination. For the treatment of MRSA infections, the administration of antibacterial agents is effective in combination with symptomatic treatment. However, it is necessary to use special antibacterial agents such as vancomycin and teicoplanin which are effective against MRSA because MRSA is resistant to common antibacterial agents. When using these agents, the dosage and period for administration should be limited to the minimum in order to prevent the emergence of new resistant strains. Currently the antibacterial agents which are used for MRSA infections require rather long period of time until they exhibit a desired effect and therefore rapid recovery of the patients cannot be expected.

In contrast to the above-described situation, a depsipeptide antibiotic named WAP-8294A$_2$ has been developed as a promising antibacterial agent (Patent Document 1). WAP-8294A$_2$ has a relatively narrow antibacterial spectrum, and it has remarkably strong antimicrobial activity against MRSA and can kill MRSA in a short period of time bactericidally. Therefore, WAP-8294A$_2$ is considered to be effective especially against acute exacerbation of MRSA infections because of its strong antibacterial action, and it is expected to be a therapeutic agent which can contribute to rapid recovery of patients in critical condition due to MRSA infections.

Patent Document 1: Japanese Patent No. 3339235

DISCLOSURE OF INVENTION

Problem which the Invention is to Solve

As mentioned above, a depsipeptide antibiotic, WAP-8294A$_2$ is anticipated as a therapeutic agent for MRSA infections which are serious problems in hospitals. Although this agent has a strong antibacterial activity, it has the drawback that it is difficult to produce an injectable formulation and solution for intravenous administration thereof which is stable at high concentrations suitable for practical use, so it was impossible to be put to practical use.

The object of the present invention is to provide an injectable formulation for extemporaneous preparation and a solution for administration of WAP-8294A$_2$ which are stable at high concentrations. The ability to produce practical injectable formulation of this antibiotic would be very useful for the treatment of MRSA infections, for which there are limited chemotherapies.

Means for Solving the Problem

WAP-8294A$_2$ is a depsipeptide antibiotic having the structural formula (I) shown below. It exerts strong antibacterial action on MRSA. WAP-8294A$_2$ is obtained as a hydrochloride, and a solution thereof is strongly acidic. The stability of an aqueous solution of WAP-8294A$_2$ depends on the pH and concentration. It is stable in an acidic condition at a low pH. However, at a neutral pH, it is viscous and tends to gel, and its stability decreases when its concentration becomes higher. Also, when there are ions such as sodium ion in an aqueous solution, it tends to gel even at a low pH and tends to form precipitates at a neutral pH.

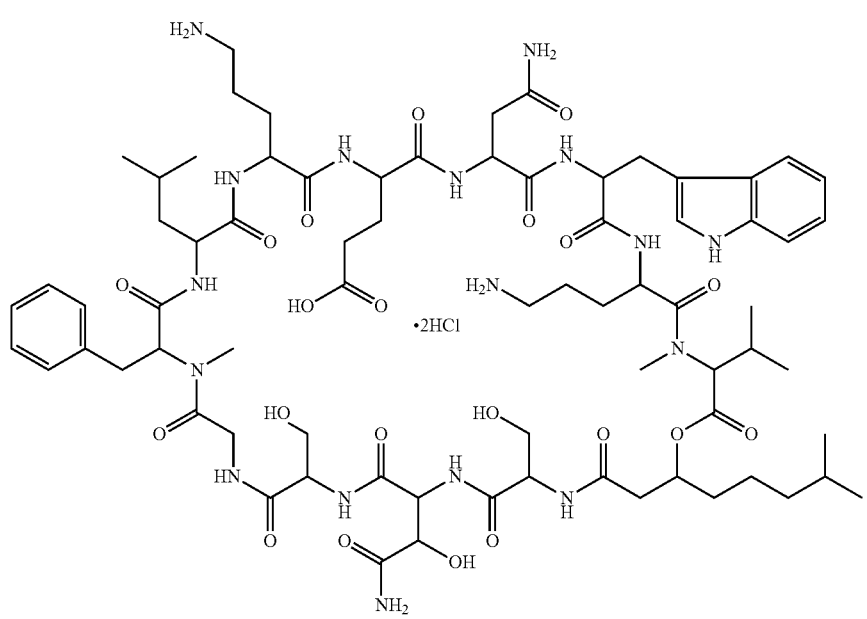

(1)

Pharmaceutical strategies have been employed in order to obtain a practical injectable solution of WAP-8294A$_2$ having the above-mentioned physical and chemical characteristics, but it has been difficult to produce a stable injectable solution containing WAP-8294A$_2$ with a high concentration. When prepared by a conventional method, an injectable solution of WAP-8294A$_2$ is an aqueous solution with low concentration. The solution is stable, but due to the increase in the required amount of the solution for administration, the burden on patients becomes heavy when the solution is injected. Also, the solution is unstable as its pH changes. Even when the pH of the solution is adjusted just before administration, it must be used soon within 2-3 hours after pH adjustment due to instability. In addition, the conventional method has the disadvantage that microprecipitates are liable to be formed in the solution near a neutral pH, and therefore the use of a filter is essential in order to prevent the precipitates from entering the blood vessels. Furthermore, there may be a danger after intravenous administration that interaction with sodium ions and/or serum proteins in the blood produces molecular aggregation to cause hematological abnormalities.

The present inventors investigated the stability of a solution of WAP-8294A$_2$. As explained below, they found that 2-hydroxypropyl-β-cyclodextrin solution and β-cyclodextrin solution are especially superior for stabilization of WAP-8294A$_2$ among solubilizers for injectable use. Further studies revealed that a stable WAP-8294A$_2$ injectable solution with a high concentration can be obtained by using these solubilizers or stabilizers and without pH adjustment, unlike in conventional methods, to prepare an injectable formulation for extemporaneous preparation.

It was also found that when a solution for administration is obtained by dilution and pH adjustment using this formulation, the solution can be prepared at a high concentration and with a small volume and is more stable than a solution prepared by a conventional method. Furthermore, the present injectable solution exhibits remarkable therapeutic effects against MRSA infection without causing hematological abnormalities after administration as shown in the below-described pharmacological experiments using animal models.

Thus, the present invention relates to an injectable formulation for extemporaneous preparation, comprising an antibiotic, WAP-8294A$_2$, of the following structural formula (1) as an active ingredient, characterized in that the formulation contains 2-hydroxypropyl-β-cyclodextrin or β-cyclodextrin as a solubilizer and the pH of the formulation is not adjusted.

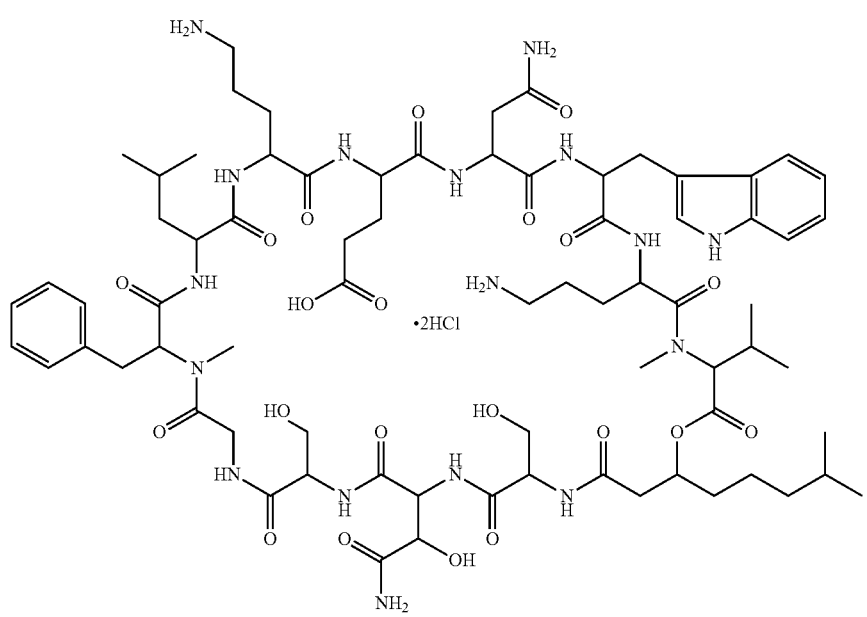

(1)

This injectable formulation is mixed with an infusion or diluent and with a pH-adjusting agent when used. The pH of the formulation preferably ranges between 2 and 4. The concentration of the antibiotic, WAP-8294A$_2$ in the formulation is preferably 5-20 mg/ml. The concentration of 2-hydroxypropyl-β-cyclodextrin in the formulation is preferably 2-50%, and the concentration of β-cyclodextrin is preferably 0.5-2.5%.

The present invention also relates to a method for preparing an injectable formulation for extemporaneous preparation, the formulation comprising an antibiotic WAP-8294A$_2$ of the following structural formula (1) as an active ingredient, characterized in that 2-hydroxypropyl-β-cyclodextrin or β-cyclodextrin is used as a solubilizer and the pH is not adjusted in preparing the formulation.

The present invention further relates to a solution for intravenous administration of an antibiotic, WAP-8294A$_2$, comprising the above-mentioned injectable formulation for extemporaneous preparation, mixed with an infusion or diluent and with a pH-adjusting agent. A preferable pH-adjusting agent used in the solution for administration is a solution of disodium hydrogen phosphate, sodium dihydrogen phosphate, and sodium hydroxide. The infusion or diluent is preferably dextrose.

The present invention additionally relates to a method for preparing a solution for intravenous administration of an antibiotic, WAP-8294A$_2$, comprising mixing the above-mentioned injectable formulation for extemporaneous preparation with an infusion or diluent and with a pH-adjusting agent.

Effects of the Invention

The injectable formulation for extemporaneous preparation off the present invention exhibits the beneficial effects of being capable of containing high concentration of WAP-8294A$_2$ and of being stable for a long period by using 2-hydroxypropyl-β-cyclodextrin or β-cyclodextrin as a solubilizer without adjusting the pH to overcome the disadvantages that an aqueous solution of WAP-8294A$_2$ is liable to gelation and is not stable.

Additionally, a solution for intravenous administration of the present invention obtained by mixing the above-mentioned injectable formulation with an infusion or diluent, and a pH-adjusting agent at the time of use is stable at a high concentration and exhibits remarkable antibacterial activity against MRSA without causing hematological abnormalities when administered.

Furthermore, since the injectable formulation of WAP-8294A$_2$ of the present invention can contain high concentration of WAP-8294A$_2$, the volume of a solution for intravenous administration can be small when administered to a patient, which makes it possible to reduce the burden on the patient.

BEST MODE FOR CARRYING OUT THE INVENTION

The injectable formulation of the present invention is prepared by dissolving an antibiotic, WAP-8294A$_2$ having the above structural formula (1) in a solution of 2-hydroxypropyl-β-cyclodextrin or β-cyclodextrin as a solubilizer or stabilizer without pH adjustment.

An antibiotic WAP-8294A$_2$ as an active ingredient has the structure represented by the above formula (1) and is isolated as a hydrochloride. Methods for production thereof include, for example, a method as described in the specification of Japanese Patent No. 3339235. This method comprises culturing an antibiotic WAP-8294A$_2$-producing bacteria belonging to Lysobacter genus such as Lysobacter sp. strain WAP-8294A (FERM BP-4990), separating the antibiotic, WAP-8294A$_2$ from the culture broth, and conducting further separation and purification to obtain the antibiotic, WAP-8294A$_2$.

Since WAP-8294A$_2$ is isolated as a hydrochloride, it is dissolved in a solution of 2-hydroxypropyl-β-cyclodextrin or β-cyclodextrin without adjusting the pH resulting in an injectable solution having a pH of 2 to 4.

The following Table 1 shows that 2-hydroxypropyl-β-cyclodextrin or β-cyclodextrin as a solubilizer or stabilizer is superior in stabilizing WAP-8294A$_2$.

TABLE 1

Stability of WAP-8294A$_2$ Solution
(preserved at room temperature)

| *preparation of solution | | results of visual observation of solution | | |
|---|---|---|---|---|
| | | day 0 | day 10 | day 80 |
| control(without additives; pH 2.8) | | ○ | ○ | Δ |
| control(pH 2.8) + 20% ethanol | | ○ | Δ | Δ |
| 0.9% sodium chloride | | Δ | Δ | X |
| pH adjustment (using sodium carbonate) | pH 3.8 | X | | |
| | pH 7.1 | X | | |
| | pH 3.8 + 20% ethanol | X | | |
| | pH 7.1 + 20% ethanol | X | | |
| buffer | 0.05M sodium acetate | Δ | X | |
| | 0.05M sodium phosphate | Δ | X | |
| sugar | 5% lactose | ○ | ○ | Δ |
| | 5% mannitol | ○ | ○ | Δ |
| | 5% sorbitol | ○ | ○ | Δ |
| cyclodextrin | 5% 2-hydroxypropyl-β-cyclodextrin | ○ | ○ | ○ |
| | 2% β-cyclodextrin | ○ | ○ | ○ |
| cation | 0.3% protamine sulfate | ○ | X | |
| | 5% glucosamine | X | | |
| | 0.3% protamine sulfate + 20% ethanol | Δ | X | |
| | 5% glucosamine + 20% ethanol | X | | |
| amino acid | 5% glycine | Δ | Δ | Δ |
| | 1% aspartic acid | ○ | ○ | Δ |
| | 1% glutamic acid | ○ | ○ | Δ |

*100 mg of WAP-8294A$_2$ is dissolved in 10 ml of each solubilizer.
○: clear, fluid,
Δ: clear, viscous,
X: cloudy, precipitation or aggregation 2-Hydroxypropyl-β-cyclodextrin contained in the injectable formulation of the present invention is preferably used within the range of 1% to 50% and more preferably 5% to 20%. The concentration of β-cyclodextrin which is used is preferably within the range of 0.5% to 2.5% and more preferably 1% to 2%.

WAP-8294A$_2$ can be dissolved in a concentration ranging from 5 mg/mL to 20 mg/mL in the injectable formulation of the present invention. More preferably, it is contained in a concentration ranging from 5 mg/mL, to 15 mg/mL. Thus, compared with a prior art method of using a solubilizer other than 2-hydroxypropyl-β-cyclodextrin and β-cyclodextrin and adjusting the pH with a pH-adjusting agent, an injectable formulation which contains high concentration of WAP-8294A$_2$ and is stable can be obtained.

The solution for intravenous administration of the present invention can be prepared by mixing the above-mentioned injectable formulation with an infusion or diluent and adding a pH-adjusting agent. This solution is preferably adjusted to a pH of 6-8. The amount of an infusion or diluent added may be suitably determined based on the concentration of WAP-8294A$_2$ in the injectable formulation, the volume suitable for administration, the dosage of WAP-8294A$_2$, etc. The solution for administration can be prepared in a relatively high concentration such as 7.5 mg/mL, and is preferably prepared in a concentration of 0.1 mg/mL, to 5 mg/mL and more preferably 0.1 mg/mL to 3 mg/mL. According to a prior art method, the obtained solution is liable to produce precipitation and is not stable even at a concentration of 0.1 mg/mL. Also, hematological disorders may be caused after administration.

Any infusion or diluent which is conventionally used can be used, but it is preferably dextrose from the standpoint of stability. As a pH-adjusting agent, a solution of disodium hydrogen phosphate, sodium dihydrogen phosphate, and sodium hydroxide is preferably used. The solution for administration of the present invention may also contain pharmaceutically conventional additives such as preservatives.

The solution for administration of the present invention can be administered as a drip infusion and is useful as an agent for treating bacterial infections, especially methicillin-resistant *Staphylococcus aureus* infection.

The dosage of the present preparation varies with the type of disease to be treated, the route of administration, the frequency of administration, the condition of the patient, etc. For example, 0.5-30 mg/kg per day of WAP-8294A$_2$ is preferably administered to an adult.

In order to further illustrate the present invention, examples and pharmacological experiments are given below, but these examples do not limit the present invention in any way.

EXAMPLE 1

Injectable Formulation of WAP-8294A$_2$ Prepared in 16% Solution of 2-hydroxypropyl-β-cyclodextrin 1.0 g of raw material of WAP-8294A$_2$ was dissolved in 200 ml of a 16% solution of 2-hydroxypropyl-β-cyclodextrin prepared using distilled water for injection to obtain an injectable formulation of WAP-8294A$_2$ without adjusting the pH. The resulting formulation was stable at room temperature for 6 months.

EXAMPLE 2

Injectable Formulation of WAP-8294A$_2$ Prepared in 5% Solution of 2-hydroxypropyl-β-cyclodextrin 1.0 g of raw material of WAP-8294A$_2$ was dissolved in 100 ml of a 5% solution of 2-hydroxypropyl-β-cyclodextrin prepared using distilled water for injection to obtain an injectable formulation of WAP-8294A$_2$ without adjusting the pH. The resulting formulation was stable at room temperature for 6 months.

EXAMPLE 3

Injectable Formulation of WAP-8294A$_2$ Prepared in 2% Solution of β-cyclodextrin 1.0 g of raw material of WAP-8294A$_2$ was dissolved in 100 ml of a 2% solution of β-cyclodextrin prepared using distilled water for injection to obtain an injectable formulation of WAP-8294A$_2$ without adjusting the pH. The resulting formulation was stable at room temperature for 6 months.

EXAMPLE 4

Preparation of Solution for Intravenous Administration of WAP-8294A$_2$ 20 ml of the injectable formulation containing 5 mg/ml of WAP-8294A$_2$ in a 16% solution of 2-hydroxypropyl-β-cyclodextrin prepared in Example 1 were neutralized by adding 2 ml of a pH-adjusting agent, which was obtained by adding 0.1 N sodium hydroxide to a phosphate buffer consisting of 39 volumes of 100 mM disodium hydrogen phosphate and 61 volumes of 100 mM sodium dihydrogen phosphate to afford final concentration of sodium hydroxide of 0.02 N. 78 ml of a 5% dextrose solution for injection were added to this solution until the total volume became 100 ml. The prepared solution for administration had a pH of 6.9 and an osmolality of 230 mOsm/kg. The resulting solution was stable at room temperature for 24 hours.

EXPERIMENTAL EXAMPLE 1

4-Day Repeated Dose Toxicity Study in Mice

Four days-repeated dose to mice was carried out and toxicity results were compared between the solution for intravenous administration of the present invention and the conventional solution in three different doses of 50 mg/kg/day, 10 mg/kg/day and 2 mg/kg/day. The injectable solution of WAP-8294A$_2$ of the present invention was prepared by the method shown in Example 4 (with 2-hydroxypropyl-β-cyclodextrin), and the prior art solution was a solution of WAP-8294A$_2$ prepared in a solution of 5% dextrose and 0.45% sodium chloride. These dosages corresponded to 7.5 mg/mL, 1.5 mg/mL and 0.3 mg/mL, respectively, as WAP-8294A$_2$.

As a result, as shown in Table 2, in the group administered 50 mg/kg/day (7.5 mg/mL as WAP-8294A$_2$) of the prior art solution, all mice died while developing clonic convulsions right after administration on day 1. In contrast, in the group administered 50 mg/kg/day of the present solution, there were no deaths or abnormality in clinical signs. As to hematological disorders, in the group administered 10 mg/kg/day (1.5 mg/mL) of the prior art solution, a tendency for a low values of erythrocytes, hemoglobin, and hematocrit, and decreased platelet values were observed. On the other hand, in the group administered 2 mg/kg/day (0.3 mg/mL) and 10 mg/kg/day (1.5 mg/mL) of the present solution, there were no abnormalities. A clear difference was observed between the prior art solution and the present solution in mortality and hematological abnormalities. Thus, the present solution of WAP-8294A$_2$ had remarkable improvement in toxicology such as an increase of the lethal dose and a reduced blood toxicity.

and vancomycin for injection (5% dextrose solution) using an MRSA infection model in mice. One hour after intravenous inoculation of MRSA (strain ATCC 33591), each single-dose of test solution was administered intravenously, and the mortality of mice was observed for a week.

The 50% effective dose (mg/kg) was calculated from the survival rate at each dosage. As shown in Table 3, the 50% effective dose of the present solution of WAP-8294A$_2$ was 52-fold lower than vancomycin. It was confirmed that the present solution for administration of WAP-8294A$_2$ showed significant efficacy against MRSA-infected mice.

TABLE 3

Comparison of efficacy in MRSA infection model in mice between the present solution of WAP-8294A$_2$ and vancomycin for injection

| test article | survival (%) in each dosage (mg/kg) | | | | | | | 50% effective dose |
|---|---|---|---|---|---|---|---|---|
| | 10 | 3.0 | 1.0 | 0.3 | 0.1 | 0.03 | 0.01 | |
| WAP-8294A$_2$ | — | 100 | 100 | 100 | 60 | 30 | 10 | 0.06 mg/kg |
| vancomycin | 100 | 30 | 0 | — | — | — | — | 3.12 mg/kg |

INDUSTRIAL APPLICABILITY

The present invention provides a stable injectable formulation containing high concentration of depsipeptide antibiotic, WAP-8294A$_2$, for preparation at the time of use. This injectable formulation is mixed with an infusion or diluent and a pH-adjusting agent at the time of use to obtain a solution for administration by injection. The resulting solution is stable at a high concentration and contributes to decreased lethal toxicity and an improvement of toxicity profile in hematology such as a decrease in erythrocytes, a decrease of blood platelets, etc. Therefore, according to the present invention, a practical formulation which fully exhibits excellent antibacterial activity of an antibiotic, WAP-8294A$_2$ is pro-

TABLE 2

Results of 4-day repeated dose toxicity study in mice (general conditions and hematological abnormality)

| | | mortality and general conditions | hematological abnormality |
|---|---|---|---|
| conventional solution | 2 mg/kg/day (0.3 mg/ml) | no abnormality | no abnormality |
| | 10 mg/kg/day (1.5 mg/ml) | no abnormality | abnormality |
| | 50 mg/kg/day (7.5 mg/ml) | all mice died | |
| solution of the present invention | 2 mg/kg/day (0.3 mg/ml) | no abnormality | no abnormality |
| | 10 mg/kg/day (1.5 mg/ml) | no abnormality | no abnormality |
| | 50 mg/kg/day (7.5 mg/ml) | no abnormality | slight abnormality |

EXPERIMENTAL EXAMPLE 2

In Vivo Efficacy Study in a MRSA Infection Model

Efficacy was compared between the present solution of WAP-8294A$_2$ prepared in the manner shown in Example 4 vided, and highly safe and extremely effective therapeutic method, especially against MRSA infections is provided.

The invention claimed is:
1. A concentrated formulation comprising the antibiotic WAP-8294A$_2$ of the following structural formula (1):

(1)

[Chemical structure of WAP-8294A₂ ·2HCl]

as an active ingredient, in a concentration of 5-20 mg/mL, and further comprising 2-hydroxypropyl-β-cyclodextrin, in an aqueous medium suitable for injection, said formulation being in the form of a concentrated, stable aqueous solution of low pH ranging between 2 and 4, said 2-hydroxypropyl-β-cyclodextrin being present in an amount of 5-50% which is effective to render the WAP-8294A₂ safe in terms of hematology and toxicology upon adjustment of pH and dilution of said concentrated aqueous solution with a solution suitable for intravenous injection or infusion.

2. The concentrated formulation as set forth in claim 1, wherein WAP-8294A₂ is present in a concentration of 5-15 mg/mL.

3. The concentrated formulation as set forth in claim 1, wherein 2-hydroxypropyl-β-cyclodextrin is present in a concentration of 5-20%.

4. The concentrated formulation as set forth in claim 2, wherein 2-hydroxypropyl-β-cyclodextrin is present in a concentration of 5-20%.

5. The concentrated formulation as set forth in claim 4, comprising 5 mg/mL of WAP-8294A₂ and a concentration of 16% 2-hydroxypropyl-β-cyclodextrin.

6. The concentrated formulation as set forth in claim 4, comprising 5 mg/mL of WAP-8294A₂ and a concentration of 5% 2-hydroxypropyl-β-cyclodextrin.

7. An intravenous solution comprising a mixture of:
(a) a concentrated formulation as set forth in claim 1;
(b) a pH-adjusting agent; and
(c) an intravenous infusion liquid or diluent;
wherein the intravenous infusion liquid or diluent and pH adjuster are present in amounts sufficient to provide a concentration of from 0.1 mg/mL to 7.5 mg/mL of WAP-8294A₂, and a pH of about 6 to 8.

8. The intravenous solution as set forth in claim 7, having a concentration of WAP-8294A₂ of from 0.1 mg/mL to 5 mg/mL.

9. The intravenous solution as set forth in claim 8, having a concentration of WAP-8294A₂ of from 0.1 mg/mL to 3 mg/mL.

10. The intravenous solution as set forth in claim 7, wherein the intravenous infusion liquid or diluent (c) is a dextrose solution.

11. The intravenous solution as set forth in claim 10, wherein the dextrose solution is 5% dextrose solution for injection.

12. The intravenous solution as set forth in claim 7, wherein the pH-adjusting agent is an aqueous solution of disodium hydrogen phosphate, sodium dihydrogen phosphate and sodium hydroxide.

13. The intravenous solution comprising a mixture of:
(a) the concentrated formulation as set forth in claim 4;
(b) a pH-adjusting agent which is an aqueous solution of disodium hydrogen phosphate, sodium dihydrogen phosphate and sodium hydroxide; and
(c) an intravenous infusion liquid or diluent which is 5% dextrose solution for injection;
the intravenous solution having a concentration of from 0.1 mg/mL to 7.5 mg/mL of WAP-8294A₂, and a pH of about 6 to 8.

14. A method for the preparation of a concentrated formulation as set forth in claim 1, said method comprising dissolving WAP-8294A₂ hydrochloride in a solution of said 2-hydroxypropyl-β-cyclodextrin in said aqueous medium suitable for injection without adjusting the pH.

15. A method for the preparation of an intravenous solution comprising mixing: (a) a concentrated formulation as set forth in claim 1; (b) a pH-adjusting agent; and (c) an intravenous infusion liquid or diluent; said intravenous infusion liquid or diluent (c) and said pH-adjusting agent (b) being added to (a) in amounts sufficient to provide a concentration of from 0.1 mg/mL to 7.5 mg/mL of WAP-8294A₂ and a pH of about 6 to 8 in the resultant intravenous solution.

16. A method for treating an infection caused by bacteria susceptible to WAP-8294A₂ comprising intravenously administering to an individual afflicted with said infection an effective antibacterial amount of an intravenous solution as set forth in claim 7.

17. The method according to claim 16, wherein said infection is a methicillin-resistant *Staphylococcus aureus* (MRSA) infection.

18. The method according to claim 16, wherein said infection is an antibiotic-resistant *Staphylococcus* infection.

* * * * *

UNITED STATES PATENT AND TRADEMARK OFFICE
CERTIFICATE OF CORRECTION

| | |
|---|---|
| PATENT NO. | : 7,968,588 B2 |
| APPLICATION NO. | : 12/306663 |
| DATED | : June 28, 2011 |
| INVENTOR(S) | : Hirofumi Nakajima et al. |

It is certified that error appears in the above-identified patent and that said Letters Patent is hereby corrected as shown below:

Title Page, left column, Item (73) (Assignee): change "eRigen Pharmaceuticals, Inc." to --aRigen Pharmaceuticals, Inc.--.

Title Page, right column, Item (57) Abstract, change the structural formula

"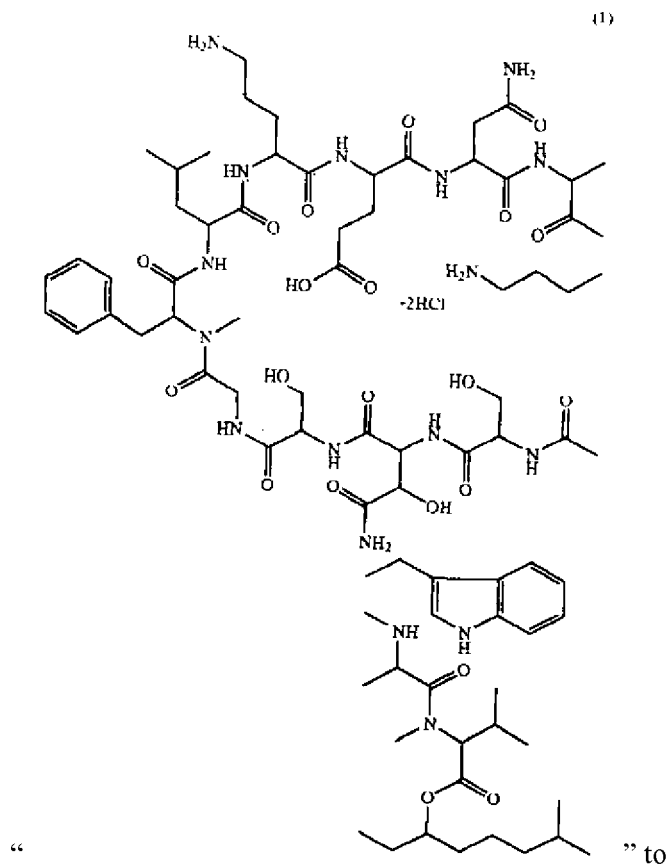" to

Signed and Sealed this
Fourth Day of October, 2011

David J. Kappos
*Director of the United States Patent and Trademark Office*

CERTIFICATE OF CORRECTION (continued)
U.S. Pat. No. 7,968,588 B2

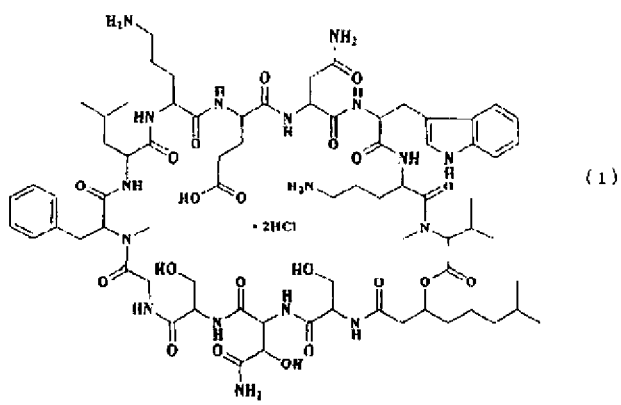

Column 11, Claim 1, change the structural formula

" 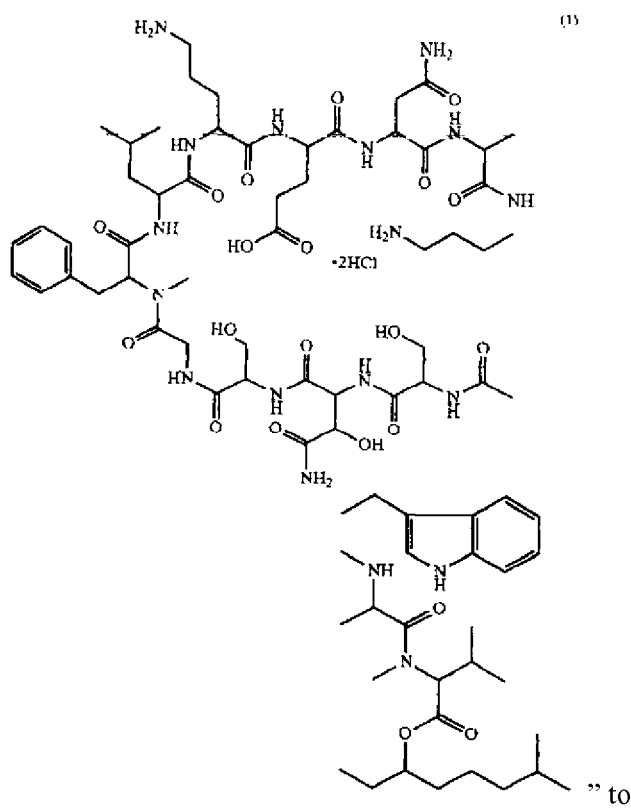 " to

" .